(12) United States Patent  
Mansfield et al.

(10) Patent No.: US 11,975,115 B2  
(45) Date of Patent: May 7, 2024

(54) PLANT TREATMENT EQUIPMENT

(71) Applicant: GOSM, Inc., Hygiene, CO (US)

(72) Inventors: Steven Dale Mansfield, Groesbeck, TX (US); Grant Donovan Orvis, Longmont, CO (US)

(73) Assignee: GOSM, INC., Hygiene, CO (US)

( * ) Notice: Subject to any disclaimer, the term of this patent is extended or adjusted under 35 U.S.C. 154(b) by 407 days.

(21) Appl. No.: 17/214,915

(22) Filed: Mar. 28, 2021

(65) Prior Publication Data

US 2021/0299287 A1    Sep. 30, 2021

Related U.S. Application Data

(60) Provisional application No. 63/001,078, filed on Mar. 27, 2020.

(51) Int. Cl.
*A61L 2/00* (2006.01)
*A61L 2/24* (2006.01)

(52) U.S. Cl.
CPC .............. *A61L 2/0011* (2013.01); *A61L 2/24* (2013.01); *A61L 2202/14* (2013.01); *A61L 2202/21* (2013.01)

(58) Field of Classification Search
CPC . A61L 2/00; A61L 2/0011; A61L 2/24; A61L 2202/14; A61L 2202/21; A01N 25/00
See application file for complete search history.

(56) References Cited

U.S. PATENT DOCUMENTS

2019/0038047 A1*  2/2019  Chi ...................... A47F 3/0408
2021/0278133 A1*  9/2021  Parker ...................... F26B 3/04

FOREIGN PATENT DOCUMENTS

WO   WO-2019133952 A2 *  7/2019 ............. A23B 7/005
WO   WO-2019160847 A2 *  8/2019 ............. F26B 21/028

* cited by examiner

*Primary Examiner* — Sean E Conley
*Assistant Examiner* — Justin Hwang

(57) ABSTRACT

A system for treating plant material uses a vessel capable of being brought to a vacuum and/or pressurized and maintained at a relatively low temperature. Plant material is placed within the vessel and the vessel draws a vacuum or is pressurized. A control system may monitor and control the creation of a vacuum, flow rate of a gas from a gas tank into the vessel, the temperature in the vessel, the flow rate of gas out of the vessel, and the pressure of the vessel.

8 Claims, 7 Drawing Sheets

PLANT TREATMENT EQUIPMENT

CLAIM OF PRIORITY

This application claims priority to and the benefit of U.S. Provisional Application 63/001,078, which was filed on Mar. 27, 2020.

INTRODUCTION

Farming is a mainstay of modern society. Plants, such as *Cannabis sativa* L. ("Cannabis") are grown, harvested, and stored in a variety of conditions. These conditions may introduce unwanted foreign elements to the plants. For example, yeast, molds, fungi, viruses, bacteria, and pests commonly infect or infest plants during growth, harvesting, and storage.

Current technology used to treat or remove these unwanted elements may damage the plant. For example, treatment protocols often involve subjecting the plant to environments with high heat, high levels of oxygen, harsh chemicals, ozone machines, and electromagnetic radiation such as ultra-violet light. These harsh environments often cause physical damage to the plant and degrade various chemical compounds that naturally occur within the plant.

In particular, cannabis flowers are often valued for the flower's physical appearance. Harsh environments can alter the physical appearance, causing the flower to appear shriveled, flattened, decolored, and/or dried. Additionally, cannabis plant material contains a variety of potentially valuable compounds. As examples, tetrahydrocannabinol (THC), cannabidiol (CBD), cannabichromene (CBC), cannabigerol (CBG), cannabinol (CBN), and other compounds are present in varying amounts in cannabis. Harsh environments can cause these and other compounds to degrade into other, potentially unwanted compounds.

Thus, it remains desirable to develop efficient methods, systems, and equipment for treating plant materials and plants, such as cannabis, without overly degrading the physical appearance or the chemical makeup of the plant material.

It is with respect to these and other considerations that aspects of the technology have been disclosed. Also, although relatively specific problems and plants have been discussed, it should be understood that the technology disclosed herein should not be limited to solving the specific problems identified in the background or the disclosure, nor be limited to specific plant types.

Plant Treatment Equipment

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

The technology described herein provides, among other aspects, a system for treating plant material that uses a vessel capable of being brought to a vacuum and/or pressurized and maintained at a relatively low pressure. Plant material, such as cannabis, is placed within the vessel and the vessel draws a vacuum or is pressurized. A control system may monitor and control the creation of a vacuum, flow rate of a gas from a gas tank into the vessel, the temperature in the vessel, the flow rate of gas out of the vessel, and the pressure of the vessel. One application is to treat plant material, such as cannabis, to reduce the viability of bacteria, viruses, and fungi.

In one example, a system for treating plant material is provided. The system may include a vessel in fluid communication with a gas tank. The system may further include a vacuum pump in fluid communication with the vessel. In aspects of the technology, the system includes an opening and a cover. The cover configured to removably engage with the opening to form a robust seal capable of substantially maintaining a low pressure in environment within the vessel.

The vessel may include a plant receiving element configured to receive plant material. Further, a vessel pressure monitor coupled to the vessel and configured to measure a pressure inside the vessel. The system may also include a first pipe having a first end and a second end that is opposite the first end. The first end may be coupled to the vessel and the second end may be coupled to the gas tank. In aspects of the technology, the first pipe configured to channel a flow of a gas between the gas tank and the vessel. The system may further include a pressure regulator coupled to the first pipe and configured to open when a pressure in the first pipe reaches above a predetermined pressure. The system of claim may also include a second pipe having a vacuum-pump end opposite a vessel end, wherein the vacuum-pump end is coupled to the vacuum pump and the vessel end is coupled to the vessel. The system may further include a flow meter coupled to the first pipe that measures at least one of the flow rate or a pressure of a gas flowing in the first pipe.

The system may also include a control system. The control system may include a computer processor in electronic communication with at least a flow meter, a vacuum flow valve, a gas tank flow valve, an exit gas flow valve, a vessel pressure monitor, and a vacuum pump. The vacuum flow valve may be coupled to the second pipe and may be configured to regulate a first flow of gas between the vacuum pump and the vessel; wherein the air tank flow valve is coupled to the first pipe and is configured to regulate a second flow of gas between an air tank and the vessel; and further wherein the exit gas flow valve is coupled to a third pipe and is configured to regulate the flow of gas out of the vessel and into a holding tank or released into the atmosphere.

The system may further include a computer processor that sends a reduce flow signal to the vacuum flow valve in response to receiving a threshold pressure signal from the vessel pressure monitor. The system may further include a temperature control element configured to regulate the gas flowing in the first pipe, wherein the temperature control element is in electronic communication with the computer processor. The system may further include a vessel temperature monitor coupled to the vessel configured to monitor a temperature of the vessel, wherein the vessel temperature monitor is in electronic communication with the computer processor. The system may also include a computer processor that sends a change temperature signal to the temperature control element in response to receiving a threshold temperature signal from the vessel temperature monitor.

In further aspects of the technology, the control system—having the at least one computer processor in electronic communication with the flow meter, the vacuum flow valve, the gas tank flow valve, the exit gas flow valve, the vessel pressure monitor, and the vacuum pump may also have computer storage media storing instructions that, when executed, performs a method to control the flow of gas in to and out of a vessel. The method may comprise receiving signals communicating the pressure of the vessel, and subsequently sending control signals to open or close, or partially open or partially close, the valves based on the receiving signals. In some examples, the method comprises: receiving a first signal indicating a first pressure monitor reading is at or above a first threshold; in response to receiving the first signal, sending a first control signal to the vacuum flow valve to cause the vacuum flow valve to at least partially open. The method may further comprise, receiving a second signal indicating the vessel pressure monitor reading is at or below the first threshold; in response to receiving the second signal, sending a second control signal to the vacuum flow valve to cause the vacuum flow valve to at least partially close; receiving at least one signal indicating the vessel pressure monitor reading is at or below the first threshold for a first count of time; after the first count of time has been exceeded, sending a third control signal to the gas tank flow valve to cause the gas tank flow valve to at least partially open to increase the pressure of the vessel. Additionally the method may further comprise, receiving a third signal indicating the vessel pressure monitor reading is at or above a second threshold; in response to receiving the third signal, sending a fourth control signal to the gas tank flow valve to cause the gas tank flow valve to at least partially close to depressurize the vessel. The method may also include receiving at least one additional signal indicating the vessel pressure monitor reading is at or above the second threshold for a second count of time; after the second count of time has been met or exceeded, sending a fifth control signal to the exit gas flow valve to release the gas to equalize the pressure with atmospheric pressure. Also, the method may include in response to sending the fifth control signal, receiving a fourth signal indicating that the vessel pressure monitor reading is at or below the second threshold, and in response to receiving the fifth control signal, sending a sixth control signal to the exit gas flow valve to cause the exit gas flow valve to at least partially close.

In aspects of the technology, the first vacuum threshold of the method to control the flow of gas in to and out of the vessel may be between about 500 Torr and about $10^{-10}$ Torr. Additionally, the first pressure threshold may be between about 25 PSI and about 250 PSI.

In examples, the technology also includes a system for treating plant material, The system may include a gas tank configured to store a gas. A vessel having a cover, wherein the vessel is in fluidic communication with the gas tank, wherein the cover is configured to removably engage with the vessel and form a robust seal therewith. The vessel may also include a plant receiving element disposed within the vessel and configured to receive plant material. The vessel may also include a vacuum pump in fluidic communication with the vessel, wherein the vacuum pump at least partially controls the flow of gas, which subsequently changes a pressure inside the vessel. The vessel may also include a vessel pressure monitor coupled to the vessel and configured to measure at least the pressure inside the vessel. The system may also include a pressure regulator coupled to the first pipe and upstream of the vessel, wherein the pressure regulator is configured to open when a pressure of channeled gas in the first pipe reaches a first threshold level.

The system may also include a second pipe having vacuum-pump end opposite a vessel end, wherein the vacuum pump end is coupled to the vacuum pump and the vessel end is coupled to the vessel. The system may also include a flow meter coupled to the first pipe, wherein the flow meter is configured to measure at least one of the flow rate or a pressure of a gas flowing in the first pipe. The system may also include a vacuum tank flow valve coupled to the second pipe and configured to regulate a first flow of gas between the vacuum pump and the vessel through the second pipe. The system may also include an air tank flow valve coupled to the first pipe and configured to regulate a second flow of gas between the air tank and the vessel through the first pipe. The system may also include an air tank exit valve coupled to the third pipe and configured to regulate a third flow of gas between the vessel and a holding tank or into the atmosphere. The system may also include a control system, the control system comprising: having a computer processor in electronic communication with at least the flow meter, the vacuum tank flow valve, the air tank flow valve, the exit gas flow valve, the vessel pressure monitor, and the vacuum pump. The system may also include a controller having a computer processor that sends a reduce flow signal to the vacuum tank flow valve in response to receiving a threshold pressure signal from the vessel pressure monitor. The system of claim may also have a temperature control element, such as a heating element, configured to regulate the temperature of the gas flowing in the first pipe, wherein the temperature control element is in electronic communication with the controller. The system may also include a vessel temperature monitor coupled to the vessel configured to monitor a temperature of the vessel, wherein the vessel control element is in electronic communication with the computer processor. The controller may send a change temperature signal to the temperature control element in response to receiving a threshold temperature signal from the vessel temperature monitor.

The technology described herein further provides a method for treating plant material. In aspects of the technology, the method comprises: placing plant material, such as cannabis, into a vessel; performing at least one cycle of depressurizing the vessel and maintaining the pressure for a period of time; returning the vessel to an atmospheric equilibrium state; and removing the plant material from the vessel. In some aspects, the at least one cycle also comprises: depressurizing the vessel to at least a first pressure; and maintaining the first pressure in the vessel within a first pressure tolerance for a first period of time.

For example, the at least one cycle of the method for treating plant material may further comprise: maintaining a first temperature in the vessel within a first temperature tolerance during at least a portion of the first period of time; after maintaining the first pressure, pressurizing the vessel to a second pressure; maintaining the second pressure in the vessel within a second pressure tolerance for a second period of time; maintaining a second temperature in the vessel within a second temperature tolerance during at least a portion of the second period of time; and after maintaining the second pressure operation, depressurizing the vessel to a third pressure.

The at least one cycle may also have the first pressure being about 500 Torr and about $10^{-10}$ Torr, and the second pressure of the at least one cycle being about 25 PSI and about 250 PSI. Further, the first pressure may be about 1 Torr and the first pressure tolerance may be about 0.5 PSI.

In some aspects of the technology, the first temperature of the at least one cycle may be between about 0° C. and about 50° C. Further, the first temperature tolerance may be about 5° C.

These and various other features as well as advantages that characterize the systems and methods described herein will be apparent from a reading of the following detailed description and a review of the associated drawings. Additional features are set forth in the description which follows. Also, additional features will be apparent from the description or may be learned by practice of the technology. The benefits and features of the technology will be realized and attained by the structure particularly pointed out in the written description and claims hereof as well as the appended drawings.

BRIEF DESCRIPTION OF THE DRAWINGS

Non-limiting and non-exclusive embodiments are described with reference to the following figures.

DETAILED DESCRIPTION

The terminology used in this disclosure is for the purpose of describing particular embodiments only and is not intended to be limiting of the disclosure. As used in the description of the embodiments of the disclosure and the appended claims, the singular forms "a," "an," and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, amount, dose, time, temperature, and the like, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this disclosure belongs.

Figure 1:
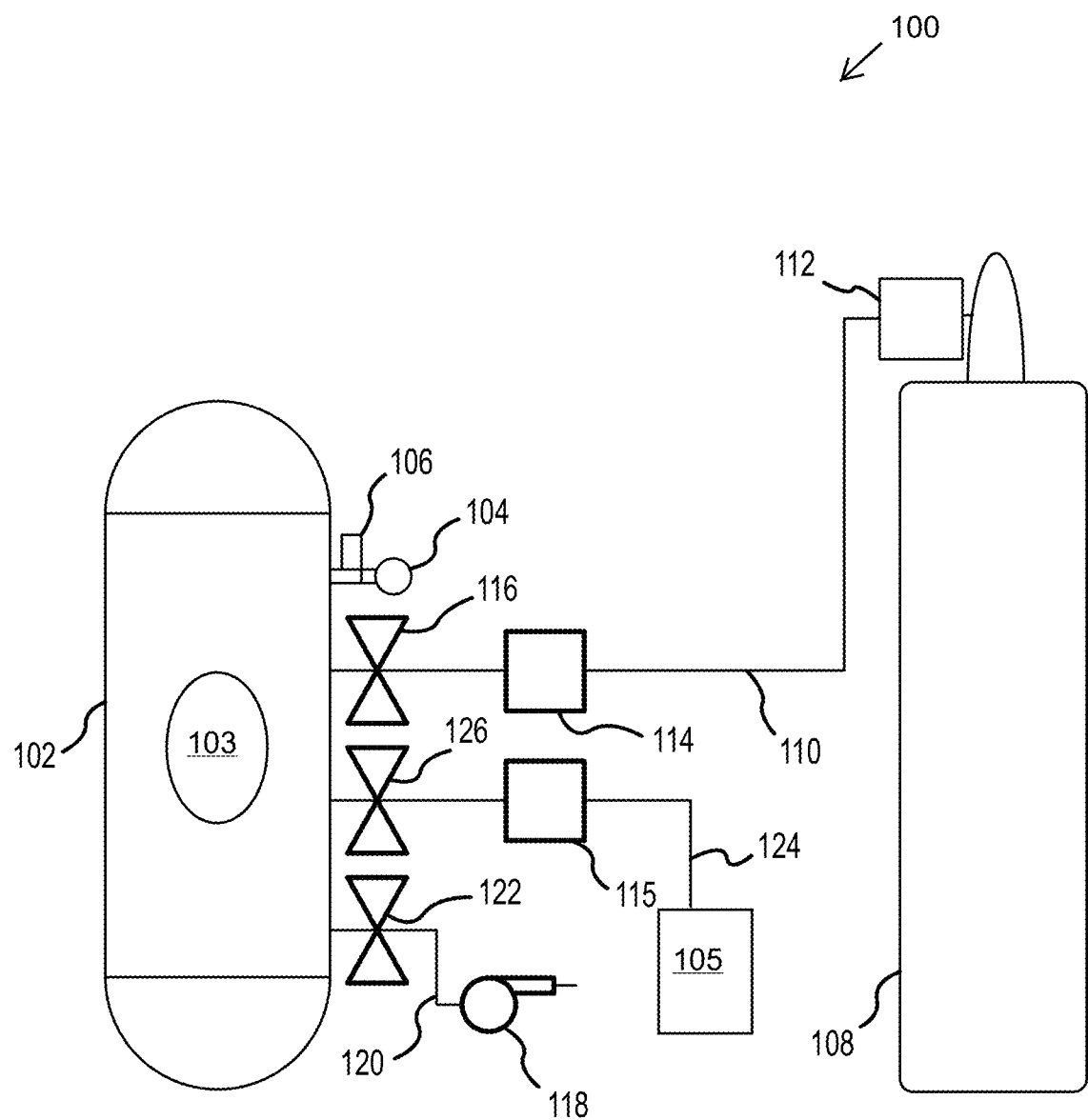
FIG. 1 illustrates an example of a system for treating plant material.

FIG. 1 illustrates an example of a system 100 for treating plant material. As illustrated, system 100 includes a vessel 102. The vessel 102 may be a variety of shapes to safely obtain and maintain pressure. As an example, the vessel 102 may be cylindrical in nature and capable of holding a pressure of up to about 150 pounds per square inch ("PSI"), up to about 250 PSI, or up to about 350 PSI for a sustained period. In aspects, the vessel 102 is a cylindrical pressure vessel with hemispherical heads at the top and the bottom. Additionally, the vessel 102 may have a variety of dimensions. As an example, the vessel 102 may be about 24 inches in length, have about a 12.75-inch diameter, and may be capped at each end with a hemispherical head having a radius of about 6 inches. The vessel 102 may be made of stainless steel, titanium, nickel alloy, carbon steel, aluminum, or any other material suitable for the technology described herein. The vessel 102 may include an opening and a cover 103 providing a doorway to the interior of the vessel 102. The opening and the cover 103 may be made of the same material or have the same specifications as the vessel 102. In some examples, the cover 103 may attach to the vessel 102 via stationary hinges allowing the opening and the cover 103 to move from an open position to a closed position. Additionally, the cover 103 may be configured to removably engage with the opening 103 to form a robust seal. The vessel 102 may include a plant receiving element, which may be designed, shaped, and configured to receive particular plant material from certain species of plants. In some examples, the plant receiving element may allow gas disposed within the interior of the vessel 102 to access, flow, or come in contact with the plant material. As a particular example, the plant receiving element may be a mesh basket capable of substantially retaining cannabis flower but allowing gas, such as $CO_2$, to come in contact with the cannabis flower. It has been observed that $CO_2$ in contact with cannabis flower in at least one low pressure/high pressure cycle inhibits microbial growth such as first pressure being about 500 Torr and about $10^{-10}$ Torr, and the second pressure of the at least one cycle being about 25 PSI and about 250 PSI.

As illustrated, coupled to the vessel 102 is a pressure monitor 104. In aspects of the technology, the pressure monitor 104 may be one of a bourdon tube type with analog-to-digital interface, a bellows gauge type with analog-to-digital interface, a strain gauge type, a piezoelectric type, or another pressure monitor that is capable of identifying the pneumatic pressure in the vessel 102 and sending a digital signal to a controller, which may be a controller as described further herein. As another example, the pressure monitor 104 may be capable of communicating a pressure in the vessel 102 to a remote location such as a remote computer, mobile device, etc. In aspects of the technology, multiple pressure monitors may be used to detect a range of pressures from near vacuum to about 350 PSI or higher.

Additionally illustrated, coupled to the vessel 102 is a vessel temperature monitor 106, which may be present. The temperature monitor 106 may be a bimetallic device, a thermocouple, an infrared sensor, a change of state sensor, or any one now known or later developed suitable for monitoring the internal temperature of the atmosphere of the vessel 102 or the plant material disposed within the vessel 102. In aspects of the technology, the temperature monitor 106 is in electronic communication with a control system, wherein the control system may have the same or similar properties as those elements described with reference to FIG. 2, to control the flow of gas and/or a temperature control element (e.g., a heating/cooling element such as a thermal jacket, a heat source, etc., to assist in the control of the temperature of the ambient atmosphere within the vessel 102 and/or the temperature of the plant material). The temperature control element may be a heating or cooling element.

As illustrated, the vessel 102 is in fluidic communication with a gas tank 108. The gas tank 108 may be any suitable tank capable of holding a gas, such as $N_2$, $O_2$, $CO_2$, or other gas. The gas held in the gas tank 108 may be pressurized. In aspects of the technology, the gas tank 108 may hold an inert gas. In certain applications, the inert gas may be preferred to prevent the degradation of the plant material or compounds contained therein. In particular, $CO_2$ may be used when the plant material is cannabis, which aids in reducing the viability of certain bacteria, fungi and yeast in certain applications, while reducing the degradation of elements of the plant.

As illustrated, a first pipe 110 provides means to place the vessel 102 in fluidic communication with the gas tank 108. One end of the first pipe 110 may be coupled to the vessel 102 and the opposite end of the first pipe 110 may be coupled to the gas tank 108. The first pipe 110 may be rigid, semi rigid, flexible, or semi flexible tubing or pipe. The first pipe 110 may be a variety of materials including steel, copper, aluminum alloy, brass, other metals, high-density polyethylene (HDPE), rubber, PVC, or any other material suitable for the technology described herein. The first pipe 110, in aspects of the technology, is used to transport gas from the gas tank 108 to the vessel 102. The first pipe 110 may be, in aspects, designed and configured to withstand a wide range of pressures, including pressures of less than about 1 PSI to pressures of more than about 250 PSI.

As illustrated, a flow meter 112 is coupled to the first pipe 110. The flow meter 112 may be implemented to monitor the flow of gas between the gas tank 108 and the vessel 102. In aspects of the technology, the flow meter 112 may be a differential pressure meter, a positive displacement meter, a mass flow meter, an anemometer, or any other meter designed and configured to monitor the flow of a gas between the gas tank 108 and the vessel 102. The flow meter 112 may be coupled to a control system, such as a control system 200 described with reference to FIG. 2, that can control the flow of gas flowing into the vessel 102. For example, the control system may receive a signal indicating a certain flow of gas from the flow meter 112. The control system may then send a signal to a control valve to actuate the valve, such as a gas tank flow valve 116.

As illustrated, system 100 further includes a first pressure regulator 114 and a second pressure regulator 115. In aspects of the technology, the first pressure regulator 114 and the second pressure regulator 115 is configured to release pressure in the system 100 should the pressure go above a pre-designated threshold. In aspects of the technology, the first pressure regulator 114 and the second pressure regulator 115 are ones of a spring-loaded valve, a balanced spring-loaded valve, dome-loaded valve, or any other regulator capable of releasing pressure. In some aspects, the first pressure regulator 114 and the second pressure regulator 115 are control valves in electronic communication with the control system, wherein the control system can send a signal to open, or partially open, one or both of the control valves to release pressure. The control valves and the control system may have the same or similar properties as those elements described with reference to FIG. 2. In some examples, the first pressure regulator 114 is configured to monitor the pressure of the first pipe 110 and the second pressure regulator 115 is configured to monitor a third pipe 124. For example, the first pressure regulator 114 may be configured to open should the pressure in the first pipe 110 go above a pre-designated threshold. Further, the second pressure regulator 115 may be configured to open should the pressure in the third pipe 124 go above a pre-designated threshold.

Aspects of the technology include the gas tank flow valve 116. In aspects of the technology, the gas tank flow valve 116 serves to control the flow of a gas from the gas tank 108 to the vessel 102. In aspects of the technology, the gas tank flow valve 116 is one of a solenoid valve, gate valve, globe valve, pinch valve, diaphragm valve, or any other valve suitable to regulate the flow of gas from the gas tank 108 to the vessel 102.

In additional aspects of the technology, a vacuum pump 118 is in fluidic communication with the vessel 102. The vacuum pump 118 is configured to draw gas out of the vessel 102. In some examples, the vacuum pump 118 is a 15-micron oil with ½ HP, 1,725 R.P.M., 115 V, 60 HZ and 7.8 A. In some applications and configurations, an oil type vacuum pump may be preferred because the oil in the pump may aid in containing contaminates pulled from the plant material.

A second pipe 120 provides gas flow out of the vessel 102 and into the environment or another vessel (e.g., a filter tank). The second pipe 120 may be used to reduce the pressure of the vessel. One end of the second pipe 120 may be coupled to the vessel 102 and the opposite end of the second pipe 120 may be coupled to the environment or other vessel. The vacuum pump 118 may aid in moving the flow of gas through the second pipe 120. The second pipe 120 may be rigid, semi rigid, flexible, or semi flexible tubing or pipe. The second pipe 120 may be a variety of materials including steel, copper, aluminum alloy, brass, other metals, high-density polyethylene (HDPE), rubber, PVC, etc. The second pipe 120 may be, in aspects, designed and configured to withstand a wide range pressures, including pressures of less than about 1 PSI to pressures of more than about 250 PSI. The second pipe 120 may be the same material or have the same specifications as the first pipe 110.

A vacuum flow valve 122 may be coupled to the second pipe 120, wherein the vacuum flow valve 122 may control flow of gas between the vacuum pump 118 and the vessel 102. In aspects of the technology, the vacuum flow valve 122 is one of a solenoid valve, a gate valve, a globe valve, a pinch valve, a diaphragm valve, or any other valve suitable to regulate the flow of gas from the vacuum flow valve 122 to the vessel 102.

In some aspects of the technology, flow of gas from the vessel 102 is drawn through the third pipe 124 to a holding tank 105 or to the atmosphere. For example, the holding tank 105 may be in fluidic communication with the vessel 102. The holding tank may be employed to off gas the vessel 102 after the vessel 102 has been in a high-pressure state. This may aid in preventing contaminants from entering the system as the vessel 102 normalizes pressure. The third pipe 124 may be rigid, semi rigid, flexible, or semi flexible tubing or pipe. The third pipe 124 may be a variety of materials including steel, copper, aluminum alloy, brass, other metals, high-density polyethylene (HDPE), rubber, PVC, etc. The third pipe 124 may be, in aspects, designed and configured to withstand a wide range of pressures, including pressures of less than about 1 PSI to pressures of more than about 250 PSI. The third pipe 124 may be the same material or have the same specifications as the first pipe 110.

An exit gas flow valve 126 may control flow of gas between the vessel 102 and the filter tank or atmosphere. In aspects of the technology, the exit gas flow valve 126 is one of a solenoid valve, a gate valve, a globe valve, a pinch valve, a diaphragm valve, or any other valve suitable to regulate the flow of gas to the exit gas flow valve 126 from the vessel 102.

Each of the pressure monitor 104, the temperature monitor 106, the gas tank flow valve 116, the vacuum flow valve 122, the exit gas flow valve 126, the vacuum pump 118 and the flow meter 112 may be in electronic communication with at least one controller, such as a controller comprising a computer processor described in further detail below.

Figure 2:
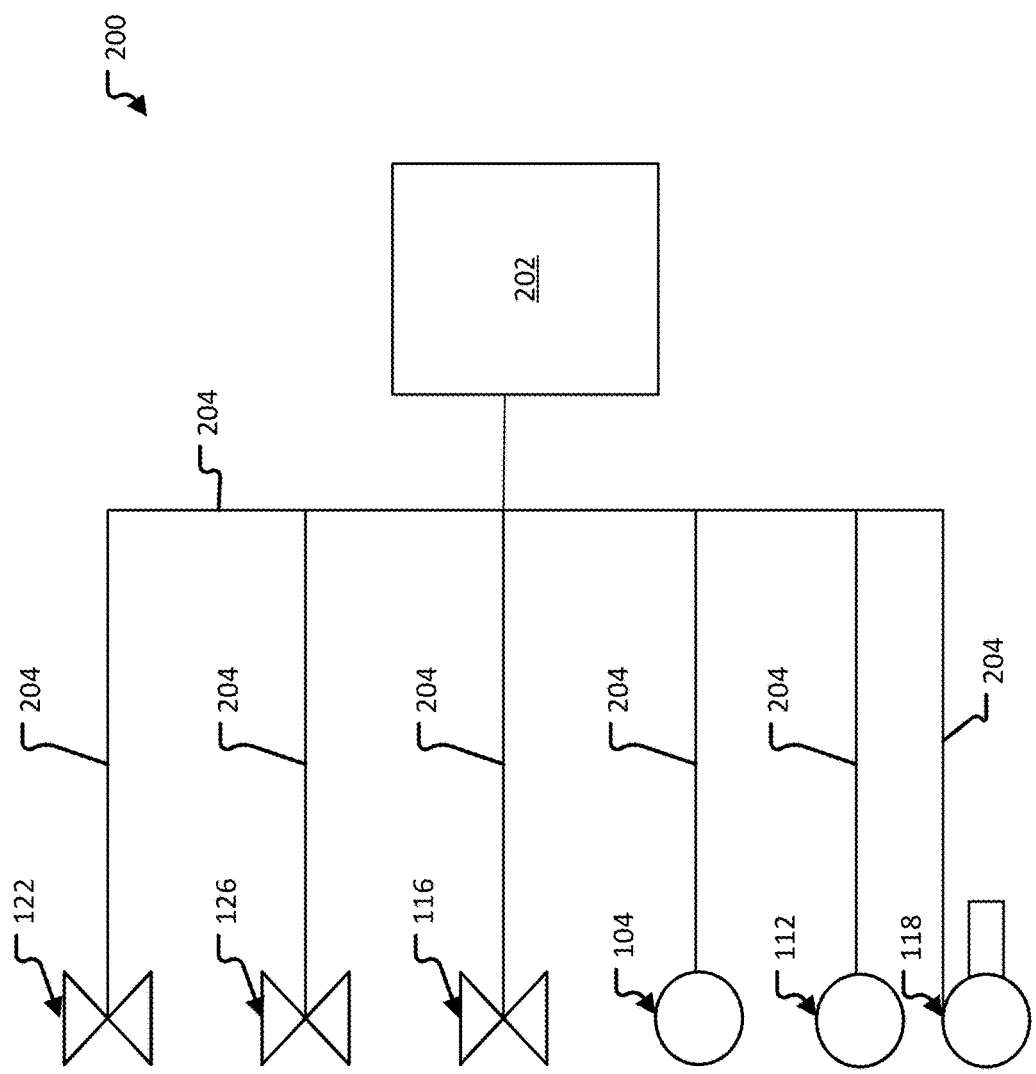
FIG. 2 illustrates an example of a control system for treating plant material.

FIG. 2 is an example of a control system 200 for treating plant material. It should be appreciated that elements of FIG. 2 having the same number as elements described with respect to FIG. 1 may have the same or similar properties as those elements described with reference to FIG. 1. A controller 202 may be in electronic communication with the vacuum flow valve 122, the gas tank flow valve 116, the exit gas flow valve 126, the pressure monitor 104, the vacuum pump 118, and the flow meter 112. Though not shown, it will be appreciated that a temperature monitor, such as temperature monitor 106, may also be in electronic communication with the controller 202.

In aspects of the technology, the controller 202 is configured to control the opening and closing of the vacuum flow valve 122, the gas tank flow valve 116, the exit gas flow valve 126, as well as the vacuum pump 118. The control may be based on signals received from the pressure monitor 104, the temperature monitor 106, and/or other monitoring devices indicating the environmental conditions within the vessel 102. The controller 202 may be a digital controller, a proportional-integral-derivative controller, a controller implemented solely via hardware, software, or any combination thereof. The controller 202 may also be in electronic communication with a temperature control. In aspects of the technology, the controller 202 may send a change temperature signal to the temperature control element in response to receiving a threshold temperature signal from a vessel temperature monitor, such as the temperature monitor 106.

As illustrated, each of the vacuum flow valve 122, the gas tank flow valve 116, the exit gas flow valve 126, the pressure monitor 104, and the flow meter 112 are in electronic communication with the controller 202 via direct electronic communication lines 204. Examples of direct electronic communication lines 204 include coaxial cables, cat5 connections, or any other electronic communication lines now known or later developed. It will be appreciated that other forms of electronic communication, such as wireless communication and BLUETOOTH® wireless communication, are anticipated such that the technology need not be limited to the use of direct electronic communication lines 204.

In aspects of the technology the controller 202 may be a computerized control system, with computer elements the same as or similar to the computers and the operating computing environments described with reference to FIGS. 4-6. For example, the controller 202 may be a control system having at least one computer processor in electronic communication with the flow meter 112, the vacuum flow valve 122, the gas tank flow valve 116, the exit gas flow valve 126, the pressure monitor 104, and the vacuum pump 118. The controller 202 may be programed to receive and interpret signals from the various devices to run through a low-pressure and/or high-pressure cycle to treat plant material.

For example, the controller 202 may begin a cycle by first receiving a signal from the pressure monitor 104 indicating that the vessel is at or above a low-pressure state. In examples, the vessel, such as vessel 102, may be pressurized to about 1 atm with $CO_2$ or some other gas from a gas tank. This pressure may be above the desired low-pressure threshold for the treatment of plants. A treatment cycle may start, as further described with reference to FIG. 3, by de-pressurizing the vessel to move the vessel to a low-pressure state. This may occur by the controller 202 sending a control signal to the vacuum flow valve 122 to cause the vacuum flow valve 122 to at least partially open. The controller 202 may send such control signal in response to receiving a signal indicating that the vessel is at a higher pressure state than is desired. For example, the pressure monitor 104 may indicate the pressure is above a threshold, a manual input may be pressed, or some other signal may be used. Additionally, the controller 202 may send a signal to the vacuum pump 118 in response to receiving a signal that the vessel pressure is above a threshold. This may cause the vacuum pump 118 to begin running and exhaust the interior vessel atmosphere. In aspects, this causes the vessel to depressurize.

A system, such as system 100, may continue to depressurize the vessel until the controller 202 receives a second signal indicating that the pressure of the vessel is in a low-pressure state. This may occur by the controller 202 receiving a signal from the pressure monitor 104 indicating that the vessel pressure is at or below the low-pressure threshold. In alternative embodiments, the gas within the vessel is evacuated for a period of time, and the controller 202 times the evacuation for that period of time through the use of a timer or a time count. That timer may send a signal to the controller 202 when the time has expired thus indicating that the vessel has been evacuated for a period of time. It will be appreciated that the controller 202 may receive one or more signals (timer, pressure monitor, etc.) indicating that the vessel is in a low-pressure state. In response to receiving signal that the vessel is in a low-pressure state (e.g., receiving a vacuum signal), the controller 202 may send a control signal to the vacuum flow valve 122 to cause the vacuum flow valve 122 to at least partially close and/or may send a signal to the vacuum pump 118 to turn off.

A digital timer or other implement may be employed to time the duration that the vessel is in the low-pressure state. Upon expiration of the timer, the controller 202 may receive one or more signals indicating the vessel has been in a low-pressure state (e.g., at or below a pressure threshold) for a first count of time. The duration of time may be determined based on treatment parameters of the plant material. After the vessel has been in the low-pressure state for a period of time (e.g., the timer has expired or a first count of time has been exceeded), the controller 202 may send a control signal to the gas tank flow 116 valve or the exit gas flow valve 126 to cause the gas tank flow valve 116 and/or the exit gas flow valve 126 to at least partially open. This may cause gas from a pressurized gas tank to flow into the vessel, which may in turn cause the pressure within the vessel to go above the low-pressure threshold, thus removing the vessel from the low-pressure state. The flow of gas may continue until the controller 202 receives a signal that the pressure in the vessel reaches or exceeds a set point. This may occur by receiving a signal from the pressure monitor 104, after a duration of time has expired, or by receiving a manual input.

For certain applications, it may be desirous to have the vessel in a high-pressure state for a duration of time after the vessel has been in a low-pressure state. In these circumstances, controller 202 may facilitate moving the vessel into a high-pressure state by leaving the gas tank flow valve 116 at least partially open until a signal is received by the controller 202 indicating that the vessel is in a high-pressure state. As one example, the controller 202 may regularly receive signals, such as from the pressure monitor 104, indicating the vessel pressure. Once the vessel pressure has reached a high-pressure threshold, the controller 202 may send a signal to the gas tank flow valve 116 to close or partially close. The vessel may then be kept in this high-pressure state for a period of time. For example, a timer or count of time may be used. After the expiration of timer or a count of time indicates the vessel has been in a high-pressure state for a period of time (which may cause a signal to be sent to a controller), the controller 202 may send a signal to at least partially open the exit gas tank valve 126. This may cause the vessel to equalize pressure with the outside atmosphere or a tank, such as the holding tank 105.

The controller 202 may continue to cycle the vessel between low-pressure states (e.g., 500 Torr and $10^{-10}$ Torr), high-pressure states (e.g., between 25 PSI and 250 PSI), and atmospheric equilibrium states (e.g., 1 atm) for one or more cycles as described herein. It will be appreciated that a partial cycle (e.g., moving the vessel into a high-pressure state or a low-pressure state only) will be desired for certain applications. It will further be appreciated that the technology provided for herein contemplates a high-pressure/low-pressure cycle, a low-pressure/high-pressure cycle, a high-pressure/equilibrium state cycle, a low-pressure/equilibrium state cycle, a high-pressure/equilibrium state/low-pressure cycle, and any combination of such cycles.

Figure 3:
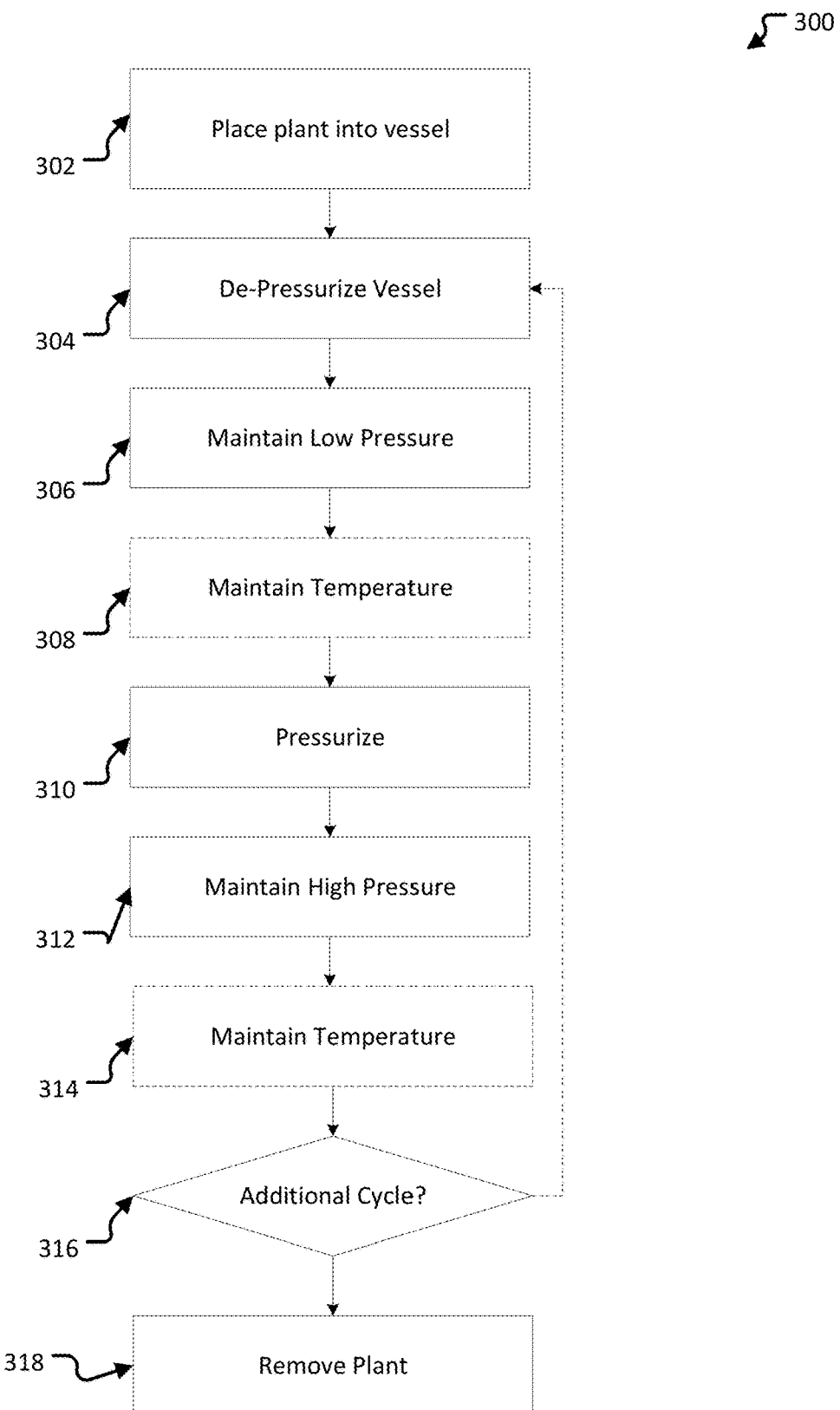
FIG. 3 is an example method for treating plant material.

FIG. 3 is a method 300 for treating plant material. Method 300 begins at operation 302, by placing plant material into a vessel. The vessel may have the same or similar properties as those elements described with reference to FIG. 1, vessel 102. In aspects, a plant material receiving element is configured to receive the plant material. The plant material receiving element may be specific for certain plants or plant materials. The plants or plant materials may be one or more of grains, nuts, seeds, berries, herbs, leaves, flowers, etc.

Method 300 then proceeds to operation 304, depressurizing the vessel to create a negative pressure differential vis-à-vis the atmosphere within the vessel. At operation 304 the vacuum is created to any one of 500 Torr, 0 Torr, $10^{-0.5}$ Torr, $10^{-1}$ Torr, $10^{-1.5}$ Torr, $10^{-2}$ Torr, $10^{-2.5}$ Torr, $10^{-3}$ Torr, $10^{-3.5}$ Torr, $10^{-4}$ Torr, $10^{-4.5}$ Torr, $10^{-5}$ Torr, $10^{-5.5}$ Torr, $10^{-6}$ Torr, $10^{-6.5}$ Torr, $10^{-7}$ Torr, $10^{-7.5}$ Torr, $10^{-8}$ Torr, $10^{-8.5}$ Torr, $10^{-9}$ Torr, $10^{-9.5}$ Torr, $10^{-10}$ Torr, any vacuum in between (within a $10^{-0.5}$ Torr tolerance), or another pressure a vessel, such as vessel 102, is capable of maintaining for any period of time. The method 300 then proceeds to operation 306 by holding the vacuum for any period. For example, it may be determined that a particular amount of time is desirous to target microbial range. For example, the period of time may be 6 hours, 12 hours, 24 hours, 36 hours, 48 hours, 60 hours, 72 hours, 80 hours, or any amount of hours in between.

In aspects of the technology, the method 300 optionally proceeds to maintain temperature operation 308. In operation 308, the temperature is maintained at or around −60° C., −45° C., −30° C., −15° C., 0° C., 2° C., 4° C., 6° C., 8° C., 10° C., 12° C., 14° C., 16° C., 18° C., 20° C., 22° C., 24° C., 26° C., 28° C., 30° C., 32° C., 34° C., 36° C., 38° C., 40° C., 42° C., 44° C., 46° C., 48° C. and/or 50° C. (+/−2° C.). The temperature may be maintained for the same period as the maintain pressure operation 306. Alternatively, the maintain temperature operation 308 may maintain the temperature for a period that is different from the period at operation 306.

Method 300 then proceeds to operation 310, pressurizing the vessel. At operation 310, the vessel is pressurized to any one of 20 PSI, 40 PSI, 60 PSI, 80 PSI, 100 PSI, 120 PSI, 140 PSI, 160 PSI, 180 PSI, 200 PSI, 220 PSI, 240 PSI, 260 PSI, 280 PSI, 300 PSI, 320 PSI, any pressure in between (within a 20 PSI tolerance), or another pressure a vessel, such as vessel 102, is capable of maintaining for any period. Method 300 then proceeds to operation 312 where the vessel maintains the pressure. In maintain pressure operation 312, the pressure is maintained at the pressure at which the vessel was pressurized at operation 310, such as 20 PSI, 40 PSI, 60 PSI, 80 PSI, 100 PSI, 120 PSI, 140 PSI, 160 PSI, 180 PSI, 200, PSI, 220 PSI, 240 PSI, 260 PSI, 280 PSI, 300 PSI, 320 PSI. The pressure may be maintained for any period. For example, the period may be 6 hours, 12 hours, 24 hours, 36 hours, 48 hours, 60 hours, 72 hours, or any amount of hours in between.

In aspects of the technology, the method 300 optionally proceeds to maintain temperature operation 314. In operation 314, the temperature is maintained at or around 0° C., 2° C., 4° C., 6° C., 8° C., 10° C., 12° C., 14° C., 16° C., 18° C., 20° C., 22° C., 24° C., 26° C., 28° C., 30° C., 32° C., 34° C., 36° C., 38° C., 40° C., 42° C., 44° C., 46° C., 48° C. and/or 50° C. (+/−2° C.). The temperature may be maintained for the same period as the maintain pressure operation 312. Alternatively, the maintain temperature operation 314 may maintain the temperature for a period that is different from the period at operation 312.

The method 300 then proceeds to de-pressure operation 315 where the vessel is depressurized. In aspects, a gas exit flow valve, such as the gas exit flow valve 126 described in FIG. 1, releases gas from the vessel until the pressure is around 1 PSI, 3 PSI, 5 PSI, 7 PSI, 9 PSI, 11 PSI, 13 PSI, 15 PSI, 17 PSI, 19 PSI, 21 PSI, or any pressure in between (+/−0.5 PSI). The pressure may be held or maintained for 0 hours 12 hours, 24 hours, 36 hours, 48 hours, 60 hours, 72 hours, or any other period, as desired or specified. In some aspects of the technology, a fan or blower or other gas moving system may be employed to circulate air about the vessel.

Optionally, method 300 may proceed to operation 316 wherein it is determined whether an additional cycle is desired. If desired, method 300 may then return to operation 304. This cycle may continue for any number of cycles, such as 1, 2, 3, 4, 5, 6, 7, 8, 9 or 10 cycles. For some applications, increasing the any number of cycles is desirous. For example, about 20, about 30, about 40, about 50, about 60, about 70, about 80, about 90, or about 100 are desirous.

The method 300 then proceeds to remove plant operation 318, where the plant material is removed from the vessel. There may be a plant collection element that holds plant material that is removed from the vessel. The plant collection element may be specific for certain plants or plant materials. As another example, the plant collection element may have a variety of holding capacities, which may be based on weight, volume, or other capacity parameter.

Figure 4A:
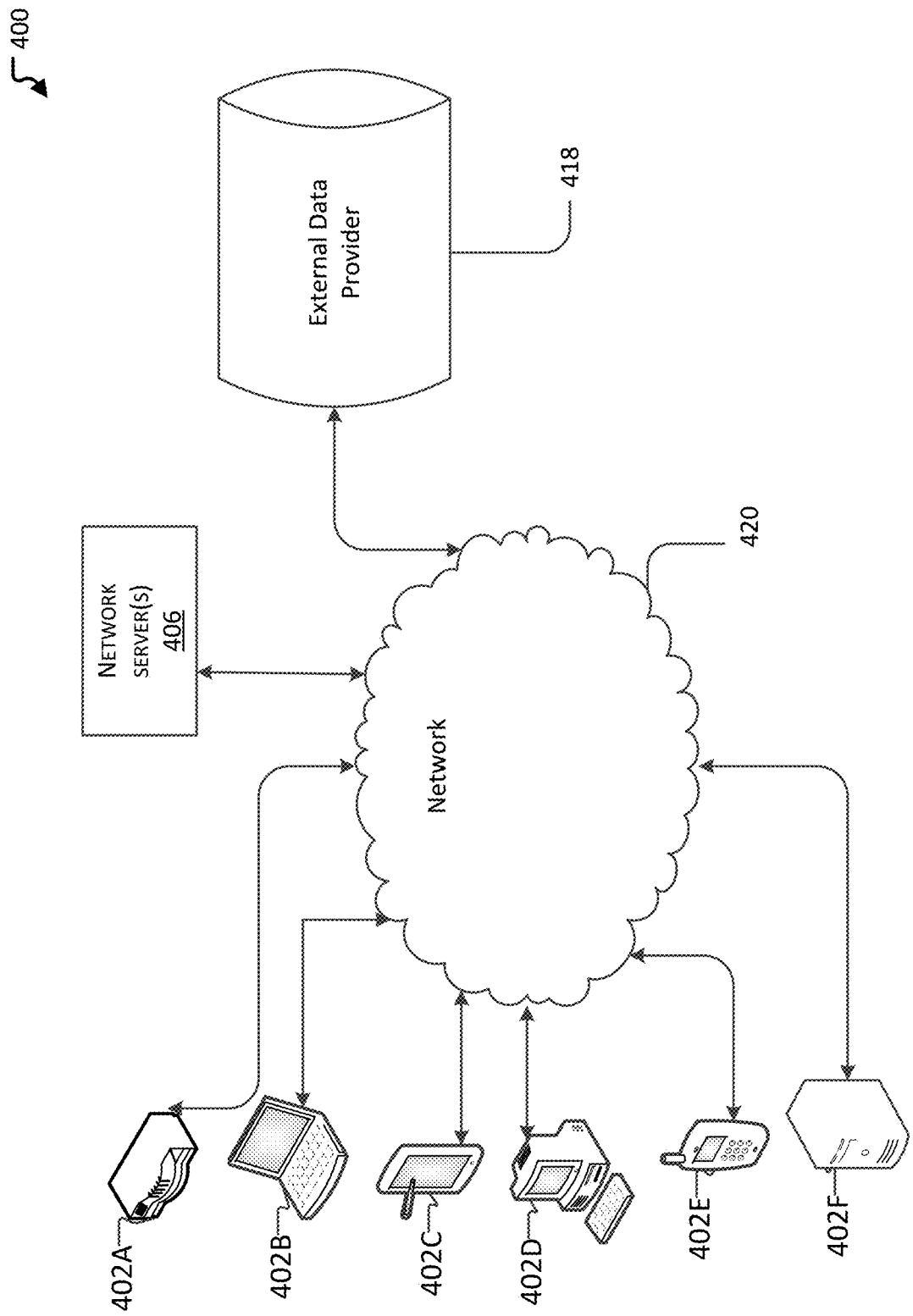
FIG. 4A is an example diagram of an operating environment in which aspects of the present technology may be practiced.

FIG. 4A is an example diagram of an operating environment 400 in which aspects of the present innovative technology, including the controller 202 described above, may be implemented. According to examples, any of computing devices, such as a modem 402A, a laptop computer 402B, a tablet 402C, a personal computer 402D, a smart phone 402E, and a server 402F, may contain modules, components, engines, etc. for controlling the various equipment associated with treating plant material. Additionally, according to aspects discussed herein, any of computing devices 402A-F may contain necessary hardware for implementing aspects of the disclosure. Any and/or all of these functions may be performed, by way of example, at network servers and/or server 406 when computing devices 402A-F request or receive data from an external data provider 418 by way of a network 420.

Figure 4B:
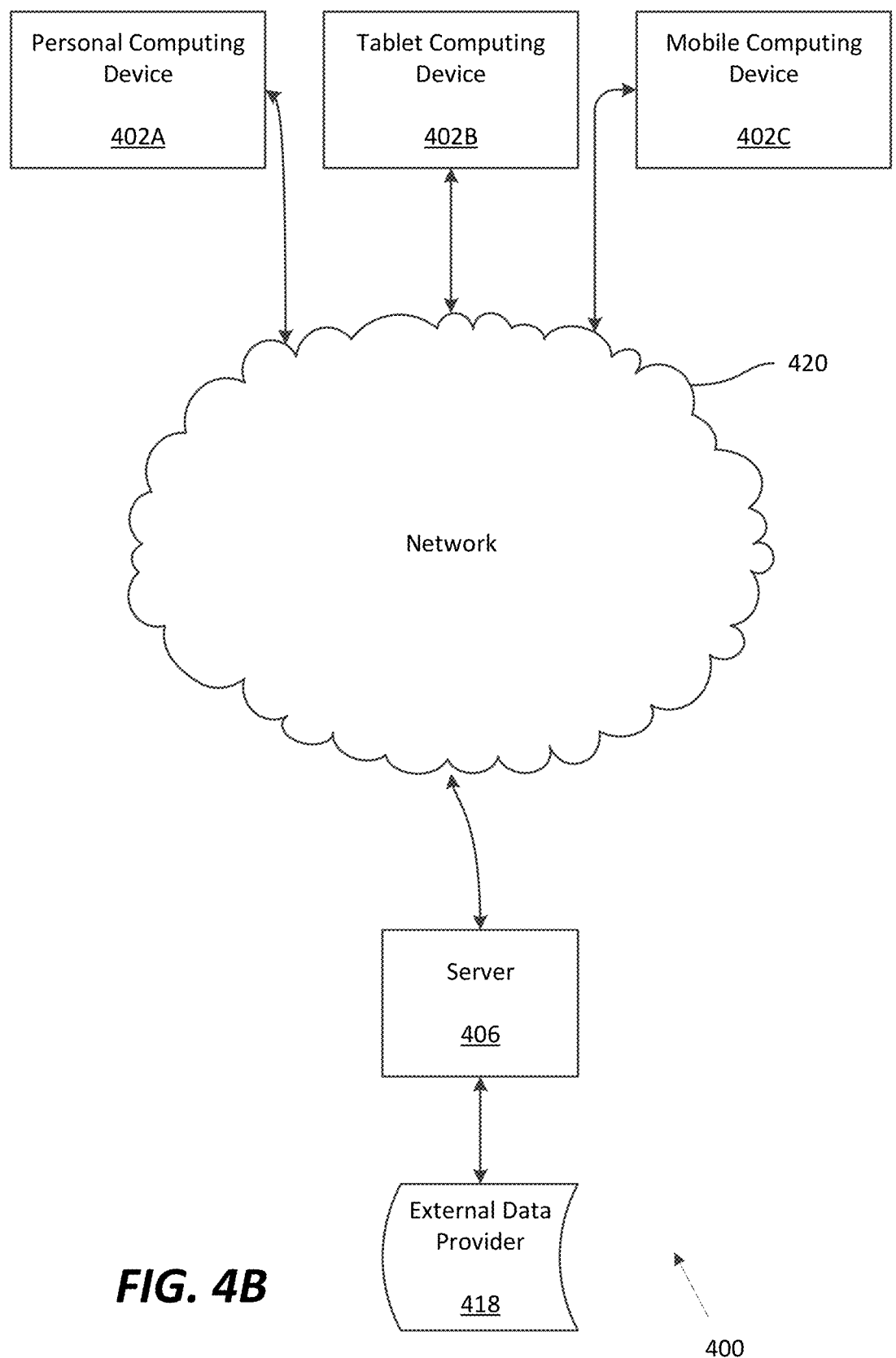
FIG. 4B is an example of the architecture of a system for performing the technology discussed herein.

Turning to FIG. 4B, one embodiment of the architecture of a system for performing the technology discussed herein is presented. Content and/or data interacted with, requested, and/or edited in association with one or more computing devices may be stored in different communication channels or other storage types. For example, data may be stored using a directory service, a web portal, a mailbox service, an instant messaging store, or a compiled networking service for controlling the various devices to treat plant material. The operating environment 400 may be used for updating information and program controls to treat plant material. The computing devices 402A, 402B, and/or 402C may provide a request to the cloud/network 420, which is then processed by the network server 406 in communication with the external data provider 418. By way of example, a client computing device may be implemented as any of the systems described herein and embodied in the personal computing device 402A, the tablet computing device 402B, and/or the mobile computing device 402C (e.g., a smart phone). Any of these aspects of the systems described herein may obtain content from the external data provider 418.

In various embodiments, the types of networks used for communication between the computing devices that makeup the present technology include, but are not limited to, an Internet, an intranet, wide area networks (WAN), local area networks (LAN), virtual private networks (VPN), GPS devices, SONAR devices, cellular networks, and additional satellite based data providers such as the Iridium satellite constellation which provides voice and data coverage to satellite phones, pagers, and integrated transceivers, etc. According to aspects of the present disclosure, the networks may include an enterprise network and a network through which a client computing device may access an enterprise network. According to additional aspects, a client network is a separate network accessing an enterprise network through externally available entry points, such as a gateway, a remote access protocol, or a public or private Internet address.

Additionally, the logical operations may be implemented as algorithms in software, firmware, analog/digital circuitry, and/or any combination thereof, without deviating from the scope of the present disclosure. The software, firmware, or similar sequence of computer instructions may be encoded and stored upon a computer readable storage medium. The software, firmware, or similar sequence of computer instructions may also be encoded within a carrier-wave signal for transmission between computing devices.

The operating environment 400 typically includes at least some form of computer readable media. Computer readable media can be any available media that can be accessed by a processor such as processing device 580 depicted in FIG. 5 and processor 602 shown in FIG. 6 or other devices comprising the operating environment 400. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

The operating environment 400 may be a single computer operating in a networked environment using logical connections to one or more remote computers. The remote computer may be a personal computer, a GPS device, a monitoring device such as a static-monitoring device or a mobile monitoring device, a pod, a mobile deployment device, a server, a router, a network PC, a peer device or other common network node, and typically includes many or all of the elements described above as well as others not so mentioned. The logical connections may include any method supported by available communications media. Such networking environments are commonplace in enterprise-wide computer networks, intranets and the Internet.

Figure 5:
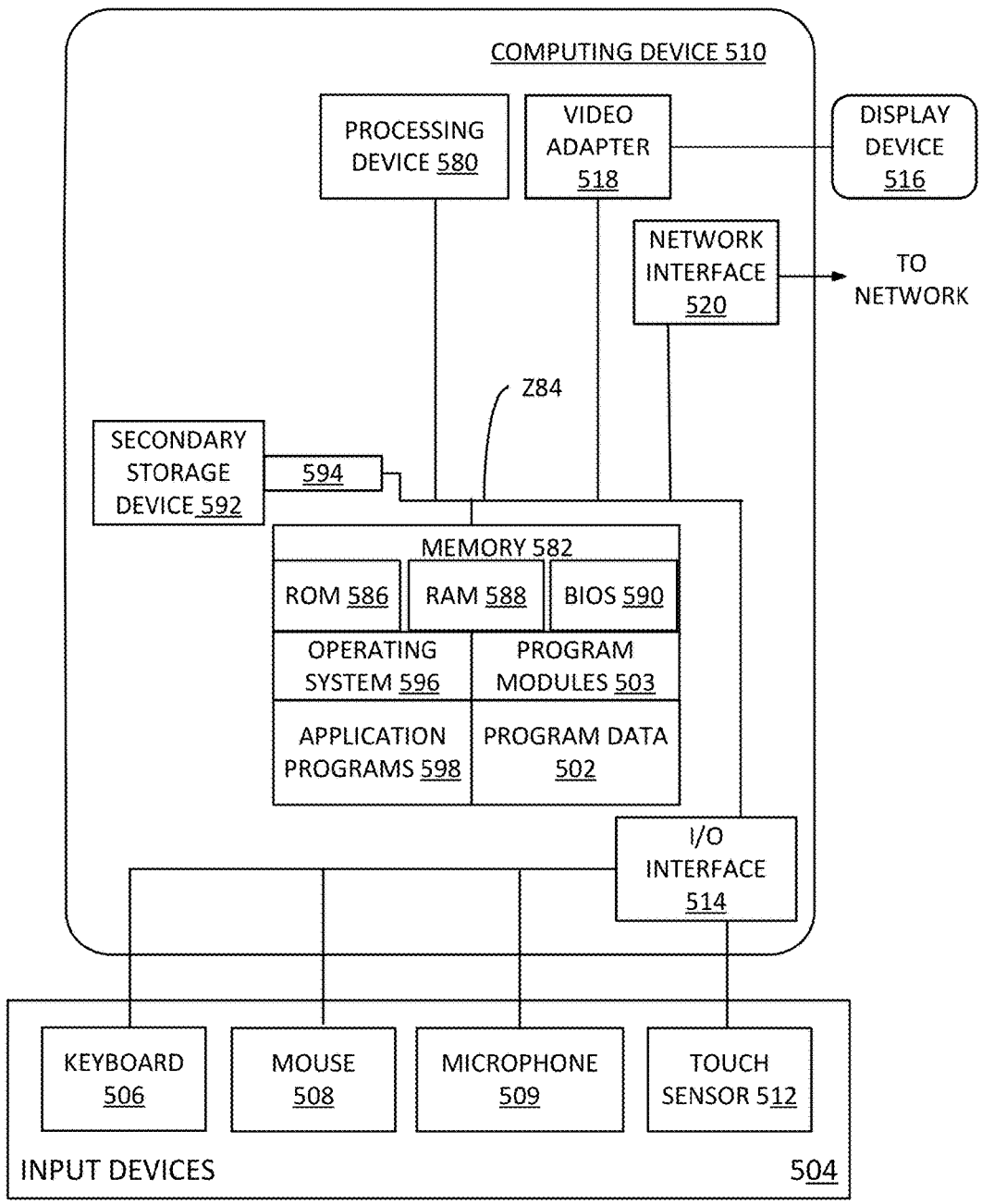
FIG. 5 is a block diagram illustrating additional physical components (e.g., hardware) of a computing device with which certain aspects of the disclosure may be practiced.

FIG. 5 illustrates one aspect of a computing system 500 in which an example architecture of a computing device 510 according to the disclosure that can be used to implement aspects of the present disclosure, including any of the plurality of computing devices described herein with reference to the various figures and their corresponding descriptions. The computing device 510 illustrated in FIG. 5 can be used to execute an operating system 596, application programs 598, and program modules 503 (including the software engines) described herein, for example, with respect to FIG. 5.

The computing device 510 includes, in some embodiments, at least one processing device 580, such as a central processing unit (CPU). A variety of processing devices are available from a variety of manufacturers, for example, Intel, Advanced Micro Devices, and/or ARM microprocessors. In this example, the computing device 510 also includes a system memory 582, and a system bus 584 that couples various system components including the system memory 582 to the at least one processing device 580. The system bus 584 is one of any number of types of bus structures including a memory bus, or memory controller; a peripheral bus; and a local bus using any of a variety of bus architectures.

Examples of devices suitable for the computing device 510 include a server computer, a pod, a mobile-monitoring device, a mobile deployment device, a static-monitoring device, a desktop computer, a laptop computer, a tablet computer, a mobile computing device (such as a smart phone, an iPod® or iPad® mobile digital device, or other mobile devices), or other devices configured to process digital instructions.

Although the exemplary environment described herein employs a hard disk drive as a secondary storage device 592, other types of computer readable storage media are used in other aspects according to the disclosure. Examples of these other types of computer readable storage media include magnetic cassettes, flash memory cards, digital video disks, Bernoulli cartridges, compact disc read only memories, digital versatile disk read only memories, random access memories, or read only memories. Additional aspects may include non-transitory media. Additionally, such computer readable storage media can include local storage or cloud-based storage.

A number of program modules can be stored in the secondary storage device 592 or the system memory 582, including the operating system 596, one or more application programs 598, other program modules 503 (such as the software engines described herein), and program data 502.

The computing device 510 can utilize any suitable operating system, such as Linux, Microsoft Windows™, Google Chrome™, Apple OS, and any other operating system suitable for a computing device.

According to examples, a user provides inputs to the computing device 510 through one or more input devices 504. Examples of input devices 504 include a keyboard 506, a mouse 508, a microphone 509, and a touch sensor 512 (such as a touchpad or touch sensitive display). Additional examples may include input devices 504 other than those specified by the keyboard 506, the mouse 508, the microphone 509 and the touch sensor 512. The input devices 504 are often connected to the processing device 580 through an input/output (I/O) interface 514 that is coupled to the system bus 584. These input devices 504 can be connected by any number of I/O interfaces 514, such as a parallel port, serial port, game port, or a universal serial bus. Wireless communication between input devices 504 and the interface 514 is possible as well, and includes infrared, BLUETOOTH® wireless technology, cellular and other radio frequency communication systems in some possible aspects.

In an exemplary aspect, a display device 516, such as a monitor, liquid crystal display device, projector, or touch sensitive display device, is also connected to the computing system 500 via an interface, such as a video adapter 518. In addition to the display device 516, the computing device 510 can include various other peripheral devices, such as speakers or a printer.

When used in a local area networking environment or a wide area networking environment (such as the Internet), the computing device 510 is typically connected to a network, such as network 420 shown in FIGS. 4A and 4B, through a network interface 520, such as an Ethernet interface. Other possible embodiments use other communication devices. For example, certain aspects of the computing device 510 may include a modem for communicating across the network. The computing device 510 typically includes at least some form of computer readable media. Computer readable media includes any available media that can be accessed by the computing device 510. By way of example, computer readable media include computer readable storage media and computer readable communication media.

The computing device 510 illustrated in FIG. 5 is also an example of programmable electronics, which may include one or more such computing devices, and when multiple computing devices are included, such computing devices can be coupled together with a suitable data communication network so as to collectively perform the various controller functions, methods, or operations disclosed herein.

Figure 6:
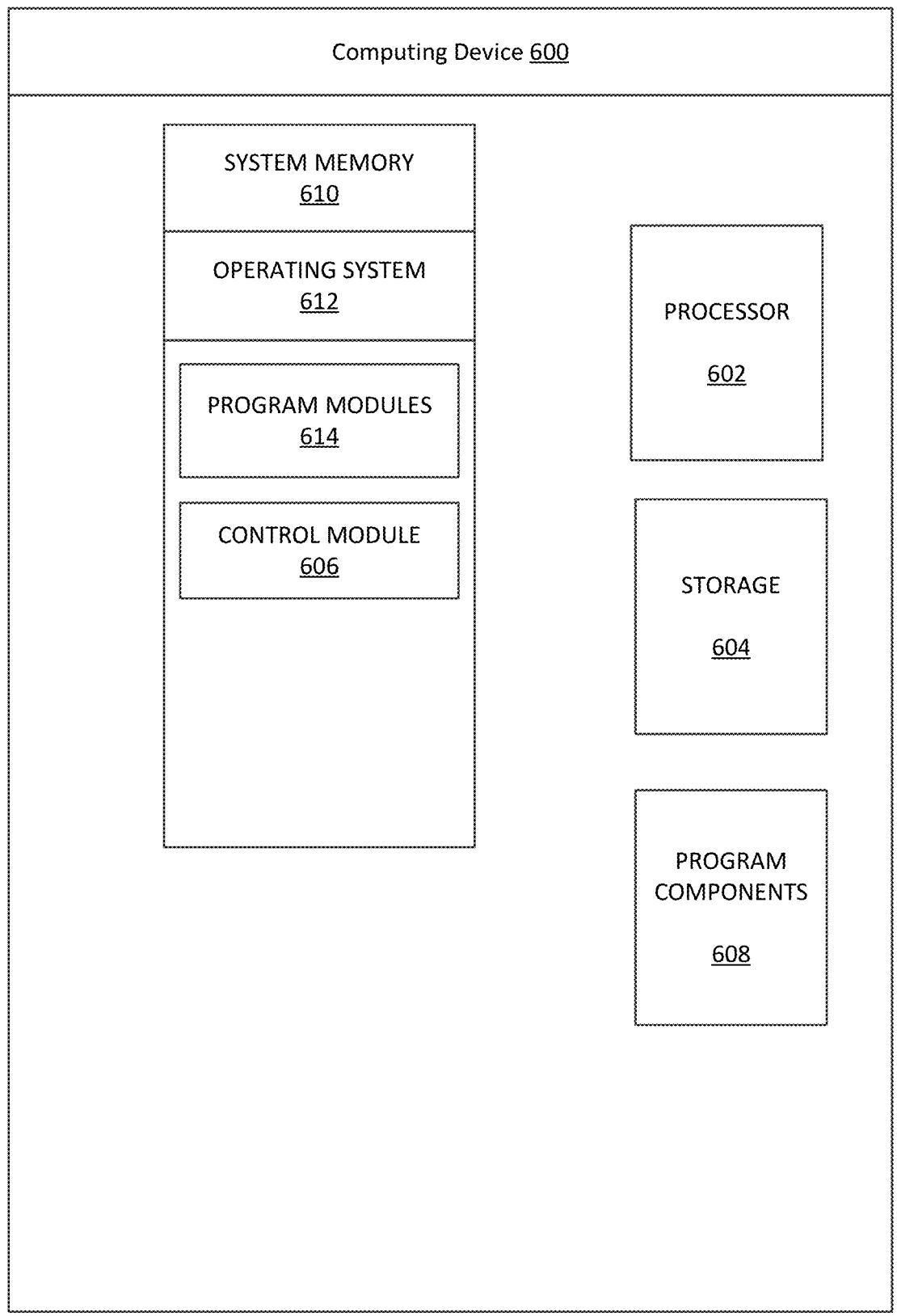
FIG. 6 illustrates one aspect in which an example architecture of a computing device according to the disclosure that can be used to implement aspects of the present disclosure, including any of the plurality of computing devices described herein with reference to the various figures and their corresponding descriptions.

FIG. 6 is a block diagram illustrating additional physical components (e.g., hardware) of another computing device 600 with which certain aspects of the disclosure may be practiced. Computing device 600 may perform these functions alone or in combination with a distributed computing network such as those described with regard to FIGS. 4A and 4B which may be in operative contact with personal computing device 402A, tablet computing device 402B and/or mobile computing device 402C which may communicate and process one or more programs 614 (which may execute controller instructions) described in FIG. 6 including the control module 606.

In a basic configuration, the computing device 600 may include at least one processor 602 and a system memory 610. Depending on the configuration and type of computing device, the system memory 610 may comprise, but is not limited to, volatile storage (e.g., random access memory, such as RAM 588), non-volatile storage (e.g., read-only memory, such as ROM 586), flash memory, or any combination of such memories. The system memory 610 may include an operating system 612 and one or more of the program modules 614. The operating system 612, for example, may be suitable for controlling the operation of the computing device 600. Furthermore, aspects of the disclosure may be practiced in conjunction with a graphics library, other operating systems, or any other application program and are not limited to any particular application or system.

The computing device 600 may have additional features or functionality. For example, the computing device 600 may also include additional data storage device (removable and/or non-removable) such as, for example, magnetic disks, optical disks, or tape. Such additional storage is illustrated in FIG. 6 by storage 604. It will be well understood by those of skill in the art that storage may also occur via the distributed computing networks described in FIG. 4A and FIG. 4B. For example, computing device 600 may communicate via network 420 in FIG. 4A and data may be stored within network server(s) 406 and transmitted back to computing device 600 via network 420 if it is determined that such stored data is necessary to execute one or more functions described herein. Additionally, computing device 600 may communicate via network 420 in FIG. 4B and data may be stored within network server(s) 406 and transmitted back to computing device 600 via network 420 if it is determined that such stored data is necessary to execute one or more functions described herein.

As stated above, a number of the program modules 614 and data files may be stored in the system memory 610. While executing the at least one processor 602, the program modules 614 (e.g., data reception module) may perform processes including using the program components (e.g., objects of a controller program), but not limited to, the aspects described herein.

The description and illustration of one or more embodiments provided in this application are not intended to limit or restrict the scope of the technology as claimed in any way. The embodiments, examples, and details provided in this application are considered sufficient to convey possession and enable others to make and use the best mode of claimed technology. The claimed technology should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the general inventive concept embodied in this application that do not depart from the broader scope of the claimed technology.

What is claimed:

1. A method for treating plant material, the method comprising:
   placing plant material into a vessel;
   performing multiple cycles, wherein each cycle of the multiple cycles comprises:
      depressurizing the vessel; and
      maintaining a pressure in the vessel within a first pressure tolerance for a period of time; and
      repressurizing the vessel by flowing a gas of $CO_2$ into the vessel from a gas tank in fluidic communication with the vessel; and wherein the multiple cycles are at least a number greater than 5 cycles;

removing the plant material from the vessel.

2. The method of claim 1, wherein the at least one cycle further comprises:

maintaining a first temperature in the vessel within a first temperature tolerance during at least a portion of the multiple cycles.

3. The method of claim 1, wherein the plant material comprises a cannabis flower containing one of cannabidiol (CBD), cannabichromene (CBC), cannabigerol (CBG), cannabinol (CBN), tetrahydrocannabinol (THC) or any combination thereof.

4. The method of claim 1, wherein the vessel is pressurized to between about 500 Torr and about $10^{-10}$ Torr during at least a portion of the multiple cycles, and the vessel is pressurized to between about 25 PSI and about 250 PSI during at least another portion of the multiple cycles.

5. The method of claim 2, wherein the vessel is pressurized to about 1 Torr within a tolerance of about 0.5 PSI during at least a portion of the multiple cycles.

6. The method of claim 2, wherein the first temperature is between about 0° C. and about 50° C.

7. The method of claim 2, wherein the first temperature tolerance is about 5° C.

8. The method of claim 1, wherein each cycle of the multiple cycles further comprises:

receiving a first signal indicating a first pressure monitor reading is at or above a first threshold;

in response to receiving the first signal, sending a first control signal to a vacuum flow valve to cause the vacuum flow valve to at least partially open;

receiving a second signal indicating the vessel pressure monitor reading is at or below the first threshold;

in response to receiving the second signal, sending a second control signal to the vacuum flow valve to cause the vacuum flow valve to at least partially close;

receiving at least one signal indicating the vessel pressure monitor reading is at or below the first threshold for a first count of time;

after the first count of time has been exceeded, sending a third control signal to a gas tank flow valve to cause the gas tank flow valve to at least partially open;

receiving a third signal indicating the vessel pressure monitor reading is at or above a second threshold;

in response to receiving the third signal, sending a fourth control signal to the gas tank flow valve to cause the gas tank flow valve to at least partially close;

receiving at least one additional signal indicating the vessel pressure monitor reading is at or above the second threshold for a second count of time;

after the second count of time has been met or exceeded, sending a fifth control signal to the exit gas flow valve;

in response to sending the fifth control signal, receiving a fourth signal indicating that the vessel pressure monitor reading is at or below the second threshold;

in response to receiving the fourth signal, sending a sixth control signal to the exit gas flow valve to cause the exit gas flow valve to at least partially close.

* * * * *